United States Patent [19]
Abe et al.

[11] Patent Number: 5,340,821
[45] Date of Patent: Aug. 23, 1994

[54] COMPOSITION AND METHOD FOR TREATING SJOEGREN SYNDROME DISEASE

[75] Inventors: Nobuaki Abe, Tokyo; Yasuyoshi Takeshita, Utsunomiya, both of Japan

[73] Assignee: Snow Brand Milk Products Co., Ltd., Japan

[21] Appl. No.: 88,304

[22] Filed: Jul. 7, 1993

[30] Foreign Application Priority Data

Jul. 10, 1992 [JP] Japan ................... 4-207485

[51] Int. Cl.$^5$ .............................. A61K 31/44
[52] U.S. Cl. ................... 514/305; 514/306; 514/825; 514/912; 514/915
[58] Field of Search ................. 514/305, 306

[56] References Cited

U.S. PATENT DOCUMENTS

| | | |
|---|---|---|
| 4,001,396 | 1/1977 | Feuer . |
| 4,100,271 | 7/1978 | Krezanoski . |
| 4,110,441 | 8/1978 | Feuer et al. . |
| 4,701,450 | 10/1987 | Kelder et al. . |
| 4,782,067 | 11/1988 | Blythin et al. ............ 514/300 |
| 4,976,969 | 12/1990 | Plamondon . |
| 4,997,654 | 3/1991 | Corsello et al. . |
| 5,162,339 | 11/1992 | Lowe, III ................. 514/305 |
| 5,242,927 | 9/1993 | Baker et al. ............. 514/299 |
| 5,242,930 | 9/1993 | Baker et al. ............. 514/305 |

OTHER PUBLICATIONS

H. B. Kaltreider, et al., "The Neuropathy of Sjogren's Syndrome", Annals of Internal Medicine, 70(4):751–762, 1969.
E. L. Alexander, et al., "Neurologic Complications of Primary Sjogren's Syndrome", Medicine, 61(4):247–257, 1982.
J. L. Konzelman, et al., "Xerostomia; Diagnosis and Treatment", U.S. Navy Medicine, 74, 16–18, 1983.
M. Navazesh, et al., "Xerostomia; Diagnosis and Treatment", Am. J. Otolaryngol, 4, 283–292, 1983.
R. I. Fox, et al., "Primary Sjogren's Syndrome; Clinical and Immunopathologic Features", Semin. Arthritis. Rheum., 14(2), 77–105, 1984.
R. T. Molina, et al., "Peripheral Inflammatory Vascular Disease In Sjogren's Syndrome", Arthritis and Rheumatism, 28(12), 1341–1347, 1985.
R. Manthorpe, et al., "Treatment of Sjogren's Syndrome; An Overview", Scand. J. Rheumatol. Suppl., 61, 237–241, 1986.
L. M. Sreebny, et al., "Xerostomia; A Neglected Symptom", Arch. Intern. Med., 147(7), 1333–1337, 1987.
H. M. Moutsopoulos, et al., "New Developments in Sjogren's Syndrome", Curr. Opin. Rheumatol., 1(3), 332–338, 1989.
K. J. Bloch, et al., "Classics in Medicine", 71(6), 386–403, 1992.

(List continued on next page.)

Primary Examiner—Marianne M. Cintins
Assistant Examiner—T. J. Criares
Attorney, Agent, or Firm—Testa, Hurwitz & Thibeault

[57] ABSTRACT

A composition for treating a Sjoegren syndrome disease is disclosed. The composition comprising derivative of spirooxathiolane-quinuclidine of the following formula (I),

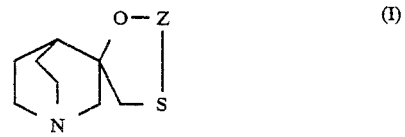

wherein Z is =$CR^1R^2$, wherein $R^1$ and $R^2$ may be the same or different and each represents hydrogen, alkyl, cyclopentyl, cyclohexyl, aryl, diarylmethylol, or alkyl which may be substituted by one or more aryl groups, or an acid addition salt thereof, or an acid addition salt thereof, as an effective component. Especially effective is an administration of a hydrochloric acid addition salt of 2-methylspiro(1,3-oxathiolane-5,3')quinuclidine.

4 Claims, 3 Drawing Sheets

OTHER PUBLICATIONS

A. Fisher, et al., "AF102B, A Novel Putative M1 Agonist As A Candidated Drug For Treatment of Alzheimer's Disease", International Symposium on Muscarinic Functions (Nov. 30–Dec. 4), 1986.

A. Fisher, et al., "AF102B A Novel Putative M1 Agonist Reverses AF64A–Induced Cognitive Impairments In Rats", Soc. Neurosci Abstr., 12 702, 1986.

A. Fisher, et al., "AF102B A Novel M1 Muscarinic Agonist A A Potential Drug For The Treatment of Alzheimer's Disease", Proceedings of the 4th Meeting of the International Study Group on the Pharmacology of Memory Disorders Associated with Aging (Jan. 16–18), 1987.

N. Nakahara, et al., "Single and Repeated Adminstration of AF102B, A Novel Muscarinic Agonist Improve Cognitive Dysfunctions in AF64A–Treated Rats", Soc. Neurosci. Abstr., 13, 837, 1987.

A. Fisher, et al., "AF102B A New M1 Agonist with Potential Application In Alzheimer's Disease", Soc. Neurosci. Abstr., 13, 657, 1987.

N. Nakahara, et al., "Effects of Intracerebroventricular Injection of Af64A On Learning Behaviors In Rats", Japan J. Pharmacol., 48(4), 121–130, 1988.

N. Nakahara, et al., "Amelioration of Experimental Amnesia (Passive Avoidance Failure) In Rodents By The Selective M1 Agonist AF102B": Japan J. Pharmacol., 48(4), 502–506, 1988.

S. Ono, et al., "Heterogeneity of Muscarinic Autoreceptors and Heteroreceptors In The Rat Brain; Effects of Novel M1 Agonist", AF102B: European J. Pharmacol., 155(½), 77–84, 1988.

F. Mizobe, et al., "AF102B A Novel Muscarinic M1 Type Agonist, Stimulated Presynaptic Auto- and Heteroreceptors In Different Potency", Trends In Pharmacol. Sci., 9(Suppl.), 81, 1988.

H. Kobayashi, et al., "Dual Type of M1 Muscarinic Effects of Selective Agonists Af102B and McN–A343 on Synaptic Gangia", Trends In Pharmacol. Sci., 9(Suppl.), 1988.

S. Mochida, et al., "Stimulation of M2–Muscarnic Receptor Decreases Calcium Entry During Action Potential", Trends In Pharmacol. Sci., 9(Supp.), 1988.

S. Hochik, et al., "Comparative Studies on Mutagenicity of Muscarnic Agonists", Mutation Res., 230, 374, 1988.

A. Fisher, et al., "AF102B A Potential Drug For The Treatment of Alzheimer's Disease (AD); Further Characterization", Soc. Neurosci. Abstr., 14, 905, 1988.

Y. Iga, et al., "SND–5008 (AF102B), A Novel Muscarinic Agonist, Improves Experimental Cognitive Dysfunctions In Rodents", Soc. Neurosci. Abstr. 14, 57, 1988.

S. Moshida, et al., "Dual Synaptic Effects of Activating M1–Muscarinic Recepotrs, In Superior Cervical Ganglia of Rabbits", Brain Research, 455, Sep. 17, 1988.

Mann Xu, et al., "Differential Effects of M1– and M2–Muscarnic Drugs on Striatal Dopamine Release and Metabolism In Freely Moving Rats": Brain Res., 495(2), 232–242, 1989.

N. Nakahara, et al., "Beneficial Effects of a Selective M1–Agonist AF102B On Experimental Models In A Possessive Avoidance Task": Japan J. Pharmacol., 49(Suppl.), 271, 1989.

M. Yoshioka, et al., "Effect of a Novel Muscarinic Receptor Agonist, AF102B, On Cardiac Sympathetic Nerve Activity In Anesthetized Rats": Japan. J. Pharmacol. 49(Suppl.), 271, 1989.

N. Nakahara, et al., "Beneficial Effects of FKS–508 (AF102B), a Selective M1 Agonist, On The Impaired Working Memory in AF64A–Treated Rats: Japan J. Pharmacol.," 51(4), 539–547, 1989.

A. Fisher, et al., "A New M1 Agonist As A Rational Strategy In Alzheimer's Disease", Alzheimer's and Parkinson's Diseases, The Second International Conference (Nov. 6–10), Kyoto, 1989.

F. Mizobe, et al., "FKS–508 (AF102B), A Novel M1 Agonist, Ameliorates Experimental Amnesia in AF6-4A–Treated Rats", Alzheimer's and Parkinson's Diseases, The Second International Conference (Nov. 6–10, Kyoto, 1989.

T. Kato, et al., "M1 Receptors Stimulate Dopamine Release Via Protein Kinase C In The Striatum of Freely Moving Rats Studies with Brain Dialysis", Alzheimer's and Parkinson's Diseases, The Second International Conference (Nov. 6–10), Kyoto, 1989.

A. Fisher, et al., "AF102B A New M1 Agonist Attenuates Cognitive Dysfunctions In AF64A–Treated Rats", Neurosci. Letters, 102(2–3), 325–331, 1989.

(List continued on next page.)

OTHER PUBLICATIONS

F. Mizobe, et al., "AF102B A Selective M1 Agonist As A Potential Drugs For The Treatment of Senile Dementia Of The Alzheimer Type", Proceedings of the Fifth Meeting of the International Study Group On The Pharmacology of Memory Disorders Associated with Aging, Zurich, Switzerland, Jan. 20–22, 1989.

A. Fisher, et al., "AF102B A Rational Treatment Strategy In Alzheimer's Disease (AD) Recent Advances", Proceedings of the Fifth Meeting of the International Study Group on the Pharmacology of Memory Disorders Associated with Aging, Zurich, Switerland, Jan. 20–22, 1989.

A. Fisher, et al., "AF102B Rational Treatment Strategy in Alzheimer's Disease (AD); Recent Advances", Adv. Neurol., 51, 257–259, 1990.

N. Nakamura, et al., "Central Muscarinic Activities of M1-Selective Agonist; Preferential Effect On Reversal of Amnesia", Brain Research 507(1), 172–175, 1990.

R. Brandeis, et al., "Reversal of Age-Related Cognitive Impairments By M1 Cholinergic Agonist AF102B", Pharmacol. Biochemi. Behav., 36(1), 89–95, 1990.

Z. Pittel, et al., "Distinct Muscarinic Receptor Subtypes Differentially Modulate Acetylcholine Release From Corticocerebral Synaptosomes": J. Neurochem., 001–008, 1990.

N. Ogane, et al., "Effects of a M1 Receptor Agonist On The Central Cholinergic System, Evaluated By a Brain Microdialysis", Neurosci Letters, 114, 95–100, 1990.

M. Yoshioka, et al., "Symphathoexcitatory Action Of A Novel Muscarine Receptor Agonist, AF102B, And Its Blockade By Pirenzapine", Pharmacol. & Toxicol., 67, 84–87, 1990.

H. Togashi, et al., "Effects of a Novel Cholinergic M1 Agonist AF102B, On Ambulation And Water Drinking Behavior In Rats", Hokkaido J. Med. Sci. 66(1), 59–66, 1990.

A. Fisher, et al., "New Muscarini Agonists With Special Emphasis On AF102B", Sec. Int. Springfield Symposium Adv. Alzheimer Therapy, Abstract, 1991.

Y. Iga, et al., "AF102B Preclinical Experience", Sec. Int. Springfield Symposium Adv. Alzheimer Therapy, Abstract, 1991.

R. Haring, et al., "Selective Agonistic Profile of AF102B In Cells Expressing Various mAchR Subtypes", Sec. Int. Springfield Symposium Adv. Alzheimer Therapy Abstract, 1991.

E. Messamore, et al., "Effort of Hepityl-Physostigmine On Cholinergic Dynamics In Rat Cerebral", Sec. Int. Springfield Symposium Adv. Alzheimer's Therapy Abstract, 1991.

N. Ogane, et al., "Do Cholinesterase Inhibitors Preferentially Inhibit Certain Molecular Forms of Brain Cholinesterase?", Sec. Int. Sprinfield Symposium Adv. Alzheimer Therapy Abstract, 1991.

A. Fisher, et al., "Racemic-cis-2-methylspiro-1,3-oxathioane-5,3'-Quinuclidine an M1 Selective Cholinergic Agonist Attenuates Cognitive Dysfunctions In An Animal Model of Alzheimer's Disease", J. Pharmacol. Exp. Ther., 257(1), 354–362, 1991.

D. Gurwitz, et al., "Selective Signal Transduction By The M1 Agonist AF102B In Cells Expressing Various Machr Subtypes", Soc. Neurosci. Abstr., 17(1—1), 388, 1991.

G. P. Vincent, et al., "AF102B, A Novel M1 Agonist, Enhanced Spatial Learning In C57BL/10 Mice With A Long Duration of Action", Brain Res., 597, 264–268, 1992.

H. Togashi, et al., "Effects of a Novel Muscarinic Receptor Agonist AF102B on Sympathoadrenomedullary Function In Rats", Jpn. J. Pharmacol., 59(Suppl.1), 170, 1992.

A. Fisher, et al., "Rigid Analogs of Acetylcholine Can Be M1-Selective Agonists Implications For A Rational Treatment Strategy In Alzheimer's Disease", Bioorg. Med. Chem. Lett., 2(8), 839–844, 1992.

M. Segal, et al., "AF102B A Muscarinic M1 Receptor Agonist Mimics Some Effects of Acetylcholine On Neurons of Rat Hippocampus Sloces", Eur. J. Pharmacol., 220(1), 103–106, 1992.

B. H. Marshall, "Lipids and Neurological Diseases", Medical Hyopthesis, 34, 272–274, 1991.

S. Shiozawa, et al., "A Preliminary Study On The Interferon-a Treatment For Xerostomia Of Sjogren's Syndrome", British J. of Rheumatology, 32, 52–54, 1993.

T. Ponge, et al., "Syndrome De Gougerot-Sjogren Primitif Avec Polymyosite Necrosante: Effet Favorable De L'Hydroxychloroquine", Rev. Neurol. (Paris), 143, 2, 147–148, 1987.

CA: vol. 112(7) No. 48812z—Fisher et al. (1980).

CA: vol. 106(21) No. 176366v—State of Israel (1987).

CA: vol. 111(19) No. 167143w—Fisher et al. (1989).

COMPOSITION AND METHOD FOR TREATING SJOEGREN SYNDROME DISEASE

BACKGROUND OF THE INVENTION

1. Field of the Invention

The present invention relates to a composition for curing Sjoegren syndrome diseases, comprising a derivative of spirooxathiolane-quinuclidine or an acid addition salt thereof as an active ingredient.

2. Description of the Background Art

Sjoegren syndrome, which is a xerotic disease caused by chronic inflammatory destruction of exocrine glands, occurs either independently or accompanied by various types of collagen diseases such as, for example, rheumatoid arthritis, systemic lupus erythematosus, progressive systemic sclerosis, polymyositis-dermatomyositis, or the like. It is an autoimmune disease which takes various pathologic forms. In addition, this disease is known to accompany lymphatic malignant tumors or quasi lymphomas at the final stage. Thus, this is a difficult-to-cure disease which attracts a great deal of attentions from medical experts. In Japan, the disease was designated as a specified disease (a difficult-to-cure disease) in 1976 by the Ministry of Health and Welfare. More recently, Tokyo metropolitan government also designated this disease as a specified disease (a difficult-to-cure disease). According to the survey made by a study team of the Ministry of Health and Welfare, the number of the patients of this disease was estimated to be 17,669 as of 1976. Nowadays, the patients is considered to have increased several times as many as in 1976, i.e., about 100,000. The disease is characterized by the fact that the number of female patients are predominant; above 90%, or the ratio of female and male patients being 38.8:1.

Irrespective of complications, the major clinical symptoms of Sjoegren syndrome are xerostomia, xerophthalmia, and xerotic keratoconjunctivitis.

There is no effective method of curing these symptoms. Symptomatic treatments, such as administration of artificial saliva, artificial tear, or respiratory tract secretion promoters, are practiced as main countermeasures. Steroidal drugs which are dosed for suppressing immune reactions are reported to be almost ineffective to these symptoms. In addition, they have unfavorable side effects. On the other hand, the systemic (e.g., oral or intravenous) administration of parasympathetic nerve (cholinergic) stimulants, conventionally known saliva and tear secretion accelerators, is gradually phasing out due to their extensive side effects. Even bethanechol, the only one cholinergic system stimulant currently used, cannot be used at all for the Sjoegren syndrome disease due to its comprehensive side effects such as headache, hot flush, palpitation, intrathoracic agony, nausea, emesis, diarrhea, abdominal discomfort, pyrosis, stomach discomfort, diaphoresis, and the like. Such a current medical situation gives the patients suffering from the Sjoegren syndrome disease conspicuous difficulty and inconvenience in carrying out the basic daily activities of living; eating, speaking, and seeing.

The object of the present invention is therefore to provide a drug for curing Sjoegren syndrome diseases which is safe and exhibits minimal toxicity as opposed to bethanechol which has extensive side effects.

In achieving this object, taking the advantage of the recent advancement in the research and development in parasympathetic nerve receptors, or cholinomimetic receptors, the inventors of the present invention synthesized and tested various chemical compounds possessing enhanced selectivity and specificity toward the central nervous system and the exocrine glands. As a result, the present inventors have discovered that derivatives of spirooxathiolane-quinuclidine, having the chemical structure of formula (I) shown below or their acid addition salts exhibit excellent effects.

SUMMARY OF THE INVENTION

Accordingly, an object of the present invention is to provide a composition for treating a Sjoegren syndrome disease comprising a derivative of spirooxathiolane-quinuclidine of the following formula,

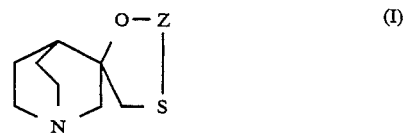

(I)

wherein Z is $=CR^1R^2$, wherein $R^1$ and $R^2$ may be the same or different and each represents hydrogen, alkyl, cyclopentyl, cyclohexyl, aryl, diarylmethylol, or alkyl which may be substituted by one or more aryl groups, or an acid addition salt thereof, as an active ingredient.

In a preferred embodiment of the present invention, said derivative of spirooxathiolane-quinuclidine, is a 2-methylspiro(1,3-oxathiolane-5,3')quinuclidine hydrochloride.

In another preferred embodiment of the present invention, said derivative of spirooxathiolane-quinuclidine is a cis-isomer of 2-methylspiro(1,3-oxathiolane-5,3')-quinuclidine hydrochloride.

Other and further objects, features and advantages of the present invention will appear more fully from the following description.

DETAILED DESCRIPTION OF THE INVENTION AND PREFERRED EMBODIMENTS

Figure 1:
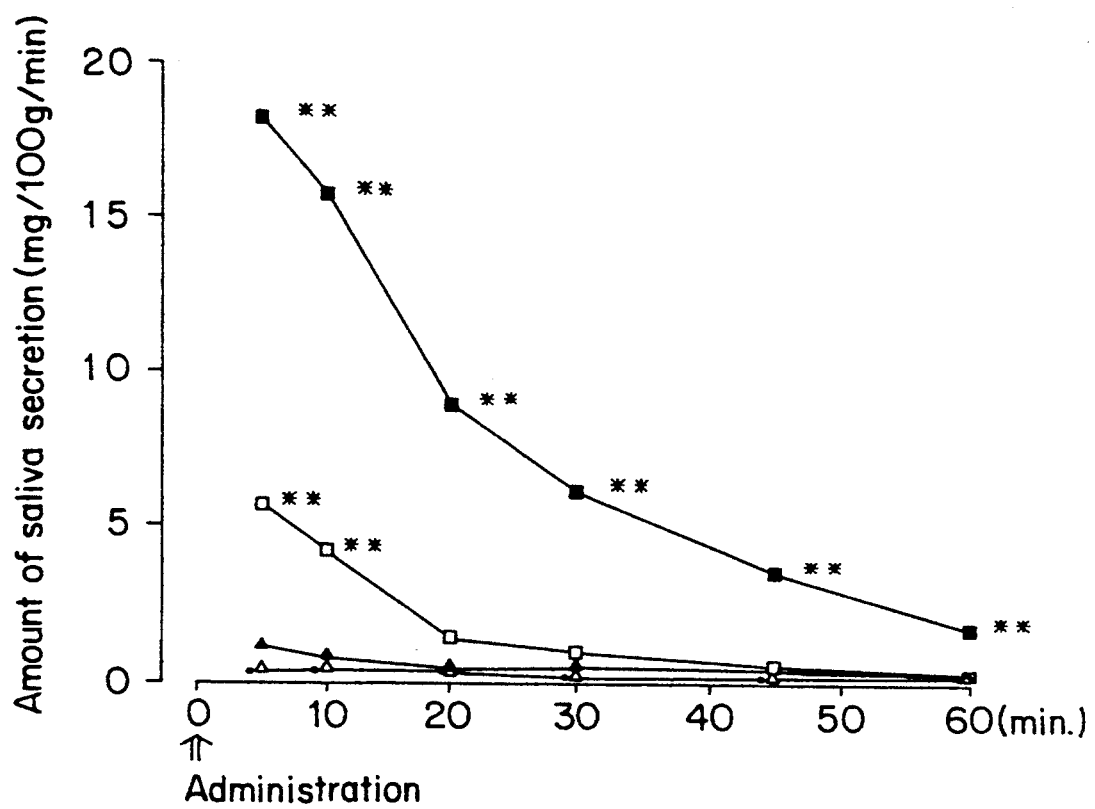
FIG. 1 is a graph showing the relationship between the time after administration of quinuclidine hydrochloride (formula (II)) and the amount of saliva secretion in Example 2, wherein -●- is a control, -△- is 0.3 mg/kg i.v., -▲- is 1.0 mg/kg i.v., -□- is 3.0 mg/kg i.v., and -■- is 10.3 mg/kg i.v., and wherein -- is a control, -△- is 0.3 mg/kg i.v., -- is 1.0 mg/kg i.v., -□- is 3.0 mg/kg i.v., and -- is 10.3 mg/kg i.v., and wherein ** indicates that the administration brings about meaningful difference at a risk factor of 1%.

In the present invention, the derivative of spirooxathiolane-quinuclidine represented by formula (I) is used as effective component in a composition for treating Sjoegren syndrome diseases. In said formula (I), as the alkyl group for $R^1$ and $R^2$ which constitute group Z, methyl, ethyl, n-propyl, and i-propyl are preferred, and phenyl group is preferred as the aryl group.

These compounds are known in the art; e.g., Japanese Patent Laid-open (kokai) No. 280497/1986. Of these derivatives of spirooxathiolane-quinuclidine, the following compounds are given as specific examples.

2-Methylspiro(1,3-oxathiolane-5,3')quinuclidine
2-Diphenylmethylspiro(1,3-oxathiolane-5,3')-quinuclidine
2-Methyl-2-phenylspiro(1,3-oxathiolane-5,3')-quinuclidine These compounds include geometrical isomers, enatiomers, diastereomers, and racemates. The effective components for the composition of the present invention may be any one of these. Acid addition salts of these compounds include either inorganic or organic acid addition salts, such as those of hydrochloric acid, sulfuric acid, phosphoric acid, sulfamic acid, lactic acid, tartaric acid, succinic acid, maleic acid, and the like.

These derivatives of spirooxathiolane-quinuclidine can be easily prepared by a method disclosed, for example, in the above-mentioned Japanese Patent Laid-open (kokai) No.280497/1986; i.e., by reacting 3-hydroxy-3-mercaptomethyl-quinuclidine with a carbonyl compound represented by the formula, $R^1$—CO—$R^2$, wherein $R^1$ and $R^2$ are the same as defined above, and separating the target compound from the reaction mixture. When the product is a mixture of optical isomers or other isomers, the isolation of each isomer can be carried out according to a method disclosed by said Japanese Patent Laid-open (kokai) No. 280497/1986 or Japanese Patent Laid-open (kokai) No. 22280/1990.

Among the derivatives of spirooxathiolane-quinuclidine, especially preferred as active component of the composition for treating Sjoegren syndrome diseases is an acid addition salt of 2-methylspiro(1,3-oxathiolane-5,3')-quinuclidine of the following formula (II).

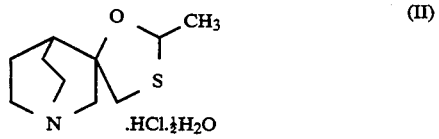

More preferred is a mixture of cis and trans isomers of this compound containing a larger amount of the cis isomer. The cis isomer is particularly preferred due to its high curing effect.

In a treatment of a Sjoegren syndrome disease with the present invention, said compound of formula (I) or a composition comprising said compound, as an effective component, and pharmaceutically acceptable carriers is administered to the patient. The composition is prepared into a form suitable for oral, parenteral, local, or rectal administration, e.g., into capsules, tablets, powder, granules, injection, ointment, eyedrop, suppositories, or the like.

As preparations suitable for oral administration, solid compositions, such as capsules, tablets, powder, granules, or troches; and liquid compositions, such as syrups or suspensions, are given as examples.

These compositions for oral administration such as capsules, tablets, and granules are prepared according to conventional methods using vehicles, for example, starch, lactose, white sugar, mannitol, carboxymethylcellulose, corn starch, inorganic salts, and the like. In addition to these vehicles, binders, disintegrators, surfactants, lubricants, fluidity accelerators, flavorers, colorants, perfumes, and the like may be added as appropriate. Specific examples of these additives include the following materials.

Binders

Starch, dextrin, gum arabic, gelatin, hydroxypropyl starch, methylcellulose, sodium carboxymethylcellulose, hydroxypropylcellulose, crystalline cellulose, ethylcellulose, polyvinylpyrrolidone, and Macrogol (trade mark).

Disintegrators

Starch, hydroxypropyl starch, sodium carboxymethylcellulose, cross-linked sodium carboxymethylcellulose, calcium carboxymethylcellulose, carboxymethylcellulose, low-substituted and hydroxypropylcellulose.

Surfactants

Sodium lauryl sulfate, soybean lecithin, sucrose fatty acid ester, and Polysolvate 80 (trademark).

Lubricants

Talc, waxes, hydrogenated vegetable oils, sucrose fatty acid ester, magnesium stearate, calcium stearate, aluminum stearate, and polyethylene glycol.

Fluidity accelerators

Light anhydrous silicic acid, dry aluminum hydroxide gel, synthetic aluminum silicate, and magnesium silicate.

The compound of formula (I) may be administered in the form of a suspension, an emulsion, a syrup, an elixir, or the like, which may contain a flavorer and a colorant.

It is desirable that these compositions contain 1–95% by weight of the effective component.

Injections are given as examples of preparation for parenteral administration.

These compositions for parenteral administration can be prepared by a conventional method. Normally, distilled water for injection, physiological saline, an aqueous solution of glucose, vegetable oil for injection, sesame oil, peanut oil, soybean oil, corn oil, propylene glycol, polyethylene glycol, and the like can be used as a diluent. In addition, a bactericidal agent, a preservative, and a stabilizer may be added as required. From the aspect of preserving the stability, such compositions for parenteral administration may be filled in vials or the like and freeze-dried by a conventional freeze-dry technique for removing water, and may be made into a liquid injection preparation immediately before use. In this instance, an isotonic agent, a stabilizer, a preservative, a soothing agent, and the like can optionally be added.

As an injection preparation, a preparation in which the active compound in a form of a salt is dissolved in conventional injection water, or a suspension or emulsion prepared using a mixture of such an active component and a pharmaceutically acceptable oil or liquid can be used. In this instance, an antibacterial agent (e.g., benzyl alcohol), an antioxidant (e.g., ascorbic acid), a buffer solution, an osmotic pressure modifier, a dissolution adjuvant, and the like may be added. It is preferable that such an injection preparation contain 0.1–5% by weight of the active component. Intravenous injection, intraarterial injection, intramuscular injection, or subcutaneous injection are applicable. Eyedrops, ointments and suppositories are given as examples of the composition for local or rectal administration.

Ointments can be prepared by adding a base component which is usually used according to a conventional method. It is preferable that such an ointment composition contain 0.5–30% by weight of the active component.

The suppositories may contain any carriers known in the art, such as polyethylene glycol, lanoline, cacao butter, fatty acid triglyceride, and the like. It is preferable that the suppository contain 1–95% by weight of the active component.

The above compositions for oral, parenteral, local or rectal administration can be prepared by a known method so as to regulate the rate of release of the active component therefrom; i.e., they may be made into a rapid release preparation, suspended release preparation, or a slow release preparation.

A dose of the composition of the present invention for curing the Sjoegren syndrome disease varies depending on the type of the composition, the manner by which it is administered, the purpose of use, the age, weight, symptoms, and the like of the patients. In general, a suitable dose for an adult, in terms of the active component contained in the composition is in the range of about 1 mg to 1 g per day. The amount of the active component in the composition can be determined depending on the intended dose. If necessary, it is possible to administer the above amount of the composition dividedly several times a day.

Other features of the invention will become apparent in the following description of the exemplary embodiment which is given for illustration of the invention and is not intended to be limiting thereof.

EXAMPLE

Example 1

Toxicity Test

Groups of ICR (CD-1) male and female mice (age: 5 weeks, weight of male mice: 22.0–33.8 g, weight of female mice: 18.8–27.3 g), each consisting of eight mice, were used for the test. 2-methylspiro(1,3-oxathiolane-5,3′)quinuclidine hydrochloride of formula (II) was orally, intravenously, or subcutaneously administered at different (high and low) doses. $LD_{50}$ (50% lethal dose) was determined by the observation of mice for two weeks thereafter. The results are shown in Table 1.

TABLE 1

| Administration route | Sex | $LD_{50}$ (mg/kg) |
| --- | --- | --- |
| Oral | Male | 139.2 |
|  | Female | 167.3 |
| Intravenous | Male | 45.2 |
|  | Female | 40.8 |
| Subcutaneous | Male | 65.0 |
|  | Female | 78.1 |

Example 2

Saliva secretion effect in rats

A pharmacological action test was carried out by using groups of Wistar male rats (weight: 150–250 g), each consisting of 5rats. The rats were anesthetized with 40 mg/kg of sodium Pentobarbital, followed by. intravenous injection of 2-methylspiro(1,3-oxathiolane-5,3′)quinuclidine hydrochloride of formula (II) in amounts of 0, 0.3, 1, 3, and 10 mg/kg. After 60 minutes, saliva secreted in oral cavity was collected by cotton balls to weigh the amount of the saliva. The results are shown in FIG. 1.

Example 3

Saliva and tear secretion effects in dogs

2-Methylspiro(1,3-oxathiolane-5,3′)quinuclidine hydrochloride of formula (II), in amounts of 0, 0.5, 3, and 18 mg/kg, was orally administered to female beagle dogs (weight: 7.1–9.6 kg) of four groups, each consisting of four dogs, one time a day and for four weeks. The secretion of saliva and tear was observed at least four times a day and the observations were recorded.

The number of animals frequently secreted saliva and tear during the four-week-period is shown in Table 2.

TABLE 2

| Animal Groups | Dose (mg/kg/day) | Number of tested animals | Number of animals secreted Saliva (%) | Tear (%) |
| --- | --- | --- | --- | --- |
| Control | 0 | 4 | 0(0) | 0(0) |
| Dose group | 0.5 | 4 | 0(0) | 0(0) |
| Dose group | 3.0 | 4 | 3(75) | 1(25) |
| Dose group | 18.0 | 4 | 4(100) | 4(100) |

Example 4

Saliva secretion effects in human

2-Methylspiro(1,3-oxathiolane-5,3′)quinuclidine hydrochloride of formula (II), in amounts of 5, 10, 20, 30, 40, 50, 60, and 70 mg, was orally administered to five men and five women, aged 20–50 years. The number of subjects who exhibited promoted secretion of saliva is shown in Table 3.

TABLE 3

| Dose (mg) | Tested subjects | Subjects showing promoted saliva secretion |
| --- | --- | --- |
| 5 | 10 | 0 |
| 10 | 10 | 0 |
| 20 | 10 | 2 |
| 30 | 10 | 8 |
| 40 | 10 | 10 |
| 50 | 10 | 10 |
| 60 | 10 | 10 |
| 70 | 10 | 10 |

Example 5

Saliva secretion effects in disease model mice

MRL/1pr mouse is a spontaneous autoimmune disease model mouse. The animal is known to exhibit lymphatic infiltration in salivary gland, the same symptom as the Sjoegren syndrome disease.

Figure 2:
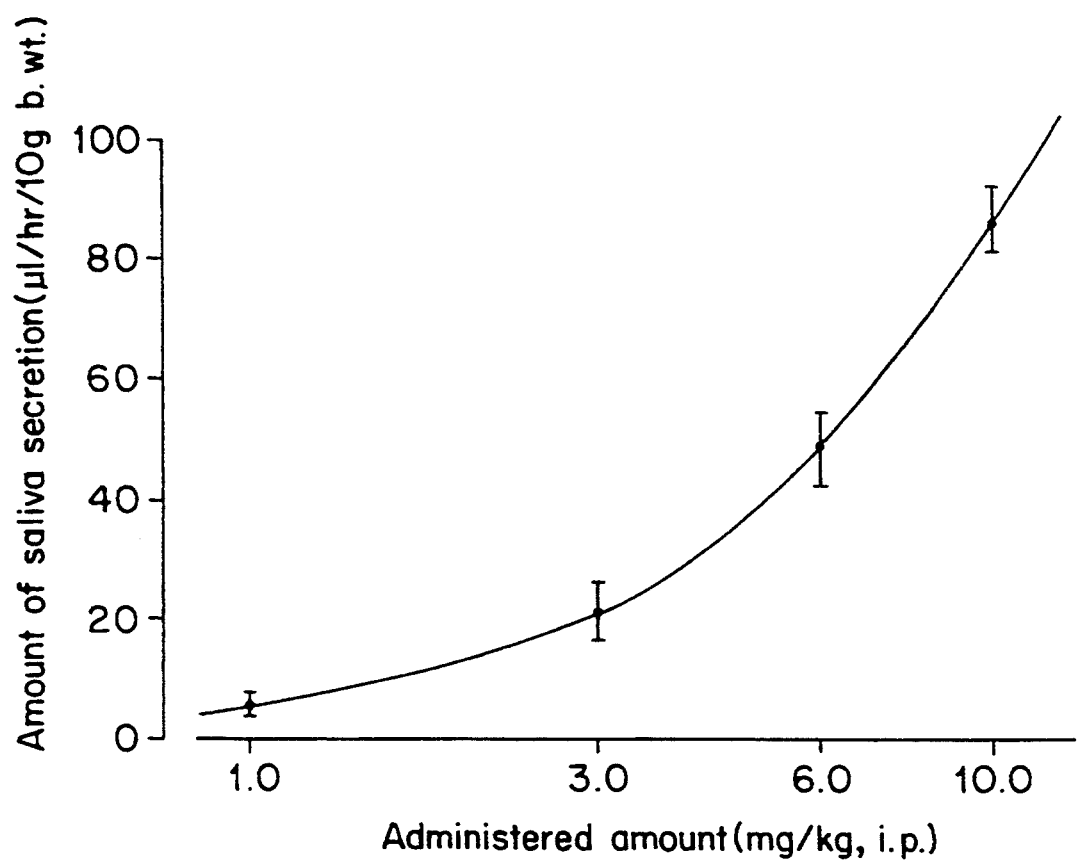
FIG. 2 is a graph showing the relationship between the amount of quinuclidine hydrochloride (formula (II)) administered to the model mouse and the total amount of saliva secretion in Example 5.
Figure 3:
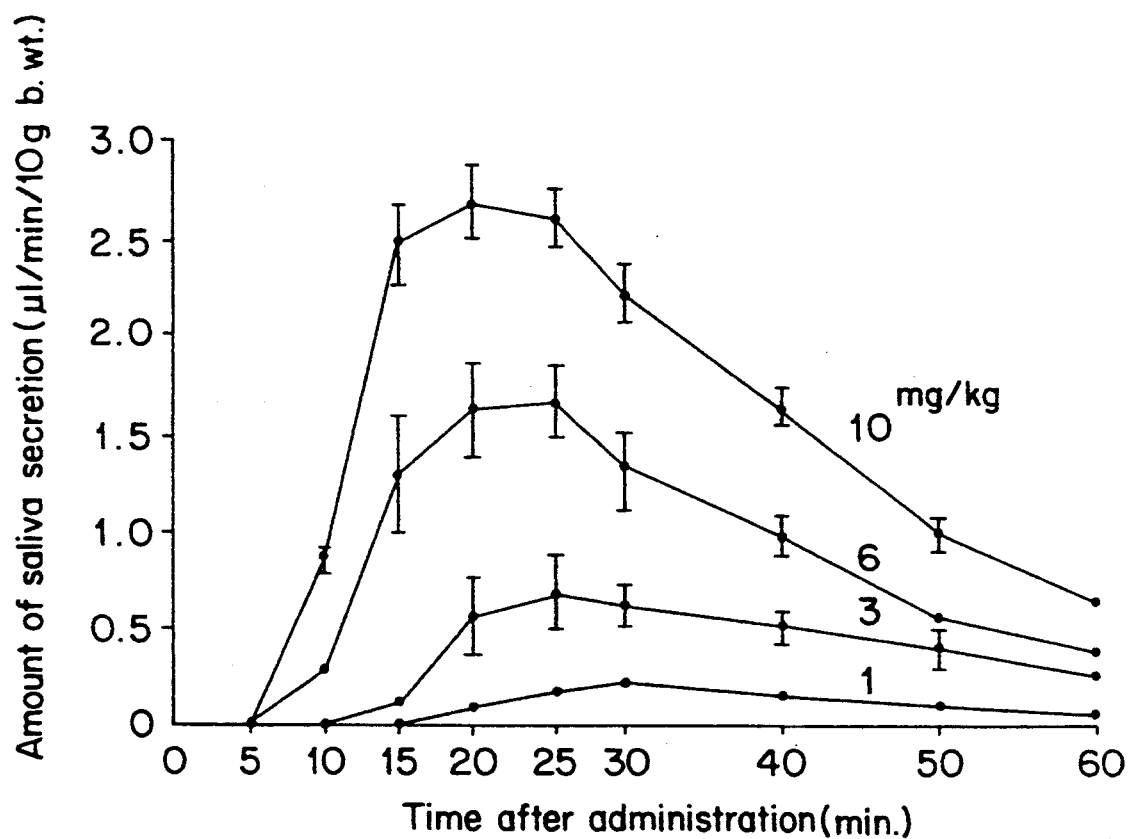
FIG. 3 is a graph showing the changes in the amount of saliva secretion with passage of time when the hydrochloric acid addition salt of quinuclidine (Formula II) was administered to the model mouse in Example 5.

A pharmaceutical action test was carried out using groups of male MRL/1pr mice, 10 weeks of age and weighing 30–38 g, each group consisting of 8 animals. The mice were anesthetized by 50 mg/kg of sodium Pentobarbital, followed by intraperitoneal injection of the 2-methylspiro(1,3-oxathiolane-5,3′)quinuclidine hydrochloride of formula (II) in amounts of 1, 3, 6, and 10 mg/kg. Saliva was collected by a micropippet placed in animal's mouth at an interval of 5 minutes for 30 minutes after the injection and an interval of 10 minutes between 30 and 60 minutes after the injection, to measure the volume of the collected saliva. The dose-dependent changes of the amount are shown in FIG. 2 and the changes with passage of time are shown in FIG. 3.

Example 6

Saliva secretion effects in a patient suffering from a Sjoegren syndrome disease Five subjects diagnosed to be suffering from a Sjoegren syndrome disease according to the diagnosis criteria made by the study team at the Ministry of Health and Welfare (M. Ofuji, Study Report Summary for 1977, the results for the year 1977 of Diagnostic criteria of Sjoegren's syndrome (Ministry of Health and Welfare's Sjoegren Investigational Research Group), M. Ofugi, Research Report of Ministry of Health and Welfare's specific disease Sjoegren Investigational Research Group in 1977, 3–6, 1978). To each subject was administered said hydrochloric acid addition salt of quinuclidine of formula (II) at a dose of 10 mg, three times a day, each time one hour before meal, for 4 weeks (the first course); 20 mg, three times a day, each time one hour before meal, for 4 weeks (the second course); and 30 mg, three times a day, each time one hour before meal, for 4 weeks (the third course). The Saxon test (Kohler P. F., Winter M. E., Arthritis Rheum, 28, 1128–1132 (1985)) for measuring the saliva secretion was performed before the start of the first course, and after the completion of the first, second, and third courses. The results are shown in Table 4.

TABLE 4

| | Amount of secreted saliva (g) | | | |
|---|---|---|---|---|
| | First course | | Second course | Third course | Observation |
| Subject | Before* | After* | After | After | of the patient |
| 1 | 0.65 | 1.08 (1.66) | 2.05 (3.15) | 3.90 (6.00) | Saliva secretion increased. |
| 2 | 0.73 | 1.24 (1.70) | 2.54 (3.48) | 4.50 (6.16) | A dry feeling of oral cavity and irritation in the eyes improved. |
| 3 | 0.76 | 1.45 (1.91) | 1.56 (2.05) | 3.65 (4.80) | The need for drinking water when taking food eliminated. |
| 4 | 0.43 | 0.65 (1.51) | 1.63 (3.80) | 2.89 (6.72) | Incidence of being awaken due to dry mouth at midnight improved. |
| 5 | 0.45 | 0.59 (1.31) | 0.97 (2.16) | 1.47 (3.27) | Saliva was felt like to secrete |

*Before: before administration; After: after administration
**The parenthesized figures are ratios to the value before the administration in the first course.

Preparation Example 1

Capsules

Capsules having the following formulation was prepared according to a conventional method.

| 2-Methylspiro(1,3-oxathiolane-5,3')quinuclidine hydrochloride (Formula II) | 10 g |
|---|---|
| Low-substitution hydroxypropylcellulose | 20 g |
| Cross-linked sodium carboxymethylcellulose | 5 g |
| Magnesium stearate | 2 g |
| Lactose | q.s. |
| | 100 g |

Preparation Example 2

Tablets

Tablets having the following formulation was prepared according to a conventional method.

| 2-Methylspiro(1,3-oxathiolane-5,3')quinuclidine hydrochloride (Formula II) | 20 g |
|---|---|
| Low-substitution hydroxypropylcellulose | 10 g |
| Crystalline cellulose | 15 g |
| Hydroxypropylmethylcellulose | 10 g |
| Magnesium stearate | 2 g |
| Lactose | q.s. |
| | 100 g |

Preparation Example 3

Injection

Injection for intravenous use having the following formulation was prepared according to a conventional method.

| 2-Methylspiro(1,3-oxathiolane-5,3')quinuclidine hydrochloride (Formula II) | 1 g |
|---|---|
| Glucose | 10 g |
| Distilled water for injection | q.s. |
| | 200 ml |

Obviously, numerous modifications and variations of the present invention are possible in light of the above teachings. It is therefore to be understood that within the scope of the appended claims, the invention may be practiced other than as specifically described herein.

What is claimed is:

1. A method for treating the symptoms of Sjoegren syndrome disease comprising administering to a patient afflicted with the disease an amount of a spirooxathiolane-quinuclide compound having the following formula (I),

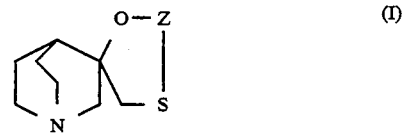

wherein Z is $=CR^1R^2$, wherein $R^1$ and $R^2$ may be the same or different and each represents hydrogen, alkyl, cyclopentyl, cyclohexyl, aryl, diarylmethylol, or alkyl which may be substituted by one or more aryl groups, or an acid addition salt thereof, sufficient to alleviate the symptoms of the disease.

2. The method of claim 1, wherein said spirooxathiolane-quinuclidine compound is a hydrochloric acid addition salt of 2-methylspiro(1,3-oxathiolane-5,3')quinuclidine having the following formula (II)

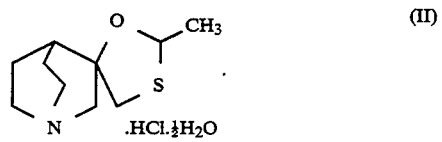

3. The method of claim 2, wherein said hydrochloric addition salt of 2-methylspiro(1,3-oxathiolane-5,3')quinuclidine is a cis isomer.

4. The method of claim 1 wherein said composition further comprises a pharmaceutically acceptable carrier.

* * * * *